United States Patent
Koyama et al.

(10) Patent No.: US 9,433,370 B2
(45) Date of Patent: Sep. 6, 2016

(54) MOISTURE METER

(75) Inventors: Miyuki Koyama, Kanagawa (JP); Keisuke Yoshino, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 524 days.

(21) Appl. No.: 13/877,090

(22) PCT Filed: Sep. 28, 2011

(86) PCT No.: PCT/JP2011/005482
§ 371 (c)(1),
(2), (4) Date: Jun. 20, 2013

(87) PCT Pub. No.: WO2012/042878
PCT Pub. Date: Apr. 5, 2012

(65) Prior Publication Data
US 2013/0274566 A1  Oct. 17, 2013

(30) Foreign Application Priority Data

Sep. 29, 2010 (JP) ................. 2010-219964

(51) Int. Cl.
*A61B 5/053* (2006.01)
*A61B 5/00* (2006.01)

(52) U.S. Cl.
CPC ............ *A61B 5/0531* (2013.01); *A61B 5/0537* (2013.01); *A61B 5/4875* (2013.01); *A61B 5/6824* (2013.01); *A61B 2562/029* (2013.01)

(58) Field of Classification Search
CPC ...... A61B 5/0059; A61B 5/01; A61B 5/443; A61B 5/0008; A61B 5/4266; A61B 5/0531; A61B 5/0537; A61B 5/4875; A61B 2562/029
USPC ............... 600/301, 306, 307, 346, 549, 547; 356/319
See application file for complete search history.

(56) References Cited

U.S. PATENT DOCUMENTS

| 5,755,672 A | 5/1998 | Arai et al. |
| 6,045,257 A | 4/2000 | Pompei et al. |

(Continued)

FOREIGN PATENT DOCUMENTS

| CN | 1244781 A | 2/2000 |
| CN | 1771004 A | 5/2006 |

(Continued)

OTHER PUBLICATIONS

International Search Report (PCT/ISA/210) issued on Dec. 13, 2011, by the Japanese Patent Office as the International Searching Authority for International Application No. PCT/JP2011/005482.

(Continued)

*Primary Examiner* — Gary Jackson
*Assistant Examiner* — Joshua Rosefelt
(74) *Attorney, Agent, or Firm* — Buchanan Ingersoll & Rooney PC

(57) ABSTRACT

Provided is a moisture meter that can easily measure a moisture content of a subject and can be effectively used as means for assisting the subject in appropriately regulating the moisture content. A moisture meter for measuring a moisture content of a subject includes: a moisture measuring unit that is held in an armpit of a subject so as to measure a moisture content of the subject, the moisture measuring unit including measurement current supply electrode portions and voltage measurement electrode portions that make contact with a skin surface of the armpit; and a temperature measuring unit that is held in the armpit of the subject so as to measure the temperature of the subject.

12 Claims, 10 Drawing Sheets

(56) References Cited

U.S. PATENT DOCUMENTS

| | | | |
|---|---|---|---|
| 6,370,426 B1* | 4/2002 | Campbell et al. | 600/547 |
| 6,459,930 B1 | 10/2002 | Takehara et al. | |
| 6,494,829 B1 | 12/2002 | New, Jr. et al. | |
| 6,643,543 B2 | 11/2003 | Takehara et al. | |
| 8,118,740 B2* | 2/2012 | Howell et al. | 600/306 |
| 2002/0022787 A1 | 2/2002 | Takehara et al. | |
| 2005/0245839 A1* | 11/2005 | Stivoric | G06F 19/3418 600/549 |
| 2007/0185392 A1* | 8/2007 | Sherman et al. | 600/306 |
| 2008/0039700 A1* | 2/2008 | Drinan et al. | 600/301 |
| 2008/0045816 A1 | 2/2008 | Jang et al. | |

FOREIGN PATENT DOCUMENTS

| | | |
|---|---|---|
| CN | 101564302 A | 10/2009 |
| DE | 10 2004 027 909 A1 | 12/2005 |
| EP | 1 891 894 A1 | 2/2008 |
| JP | 10-71130 A | 3/1998 |
| JP | H11318845 A | 11/1999 |
| JP | 2001170088 A | 6/2001 |
| JP | 2002-045346 A | 2/2002 |
| JP | 2003-525653 A | 9/2003 |
| JP | 3699640 B2 | 9/2005 |
| JP | 2005287547 A | 10/2005 |
| JP | 3977983 B2 | 9/2007 |
| JP | 2008-167933 A | 7/2008 |
| JP | 2009-153727 A | 7/2009 |
| WO | 2004028359 A1 | 4/2004 |

OTHER PUBLICATIONS

Office Action issued on Oct. 31, 2014, by the Chinese Patent Office in corresponding Chinese Patent Application No. 201180047586.1 (6 pgs).

Russian Office Action issued Aug. 19, 2015, by the Russian Patent Office, in corresponding Russian Patent Application No. 2013119266/14 (028481) with English translation of Russian Office Action (9 pages).

Suibun Bunpu to Sono Ouyo, Estimation of Fluid Distribution by Impedance Method, Japanese Journal of Medical Electronics and Biological Engineering, vol. 23, No. 6, 1985 (with English abstract).

Office Action (Official Notification of Examination) issued on Dec. 1, 2015, by the Taiwanese Patent Office in corresponding Taiwanese Patent Application No. 101109978, and an English Translation of the Office Action. (9 pages).

\* cited by examiner

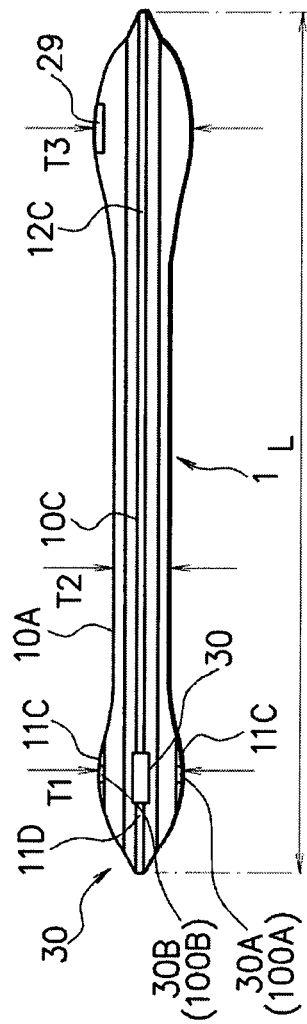
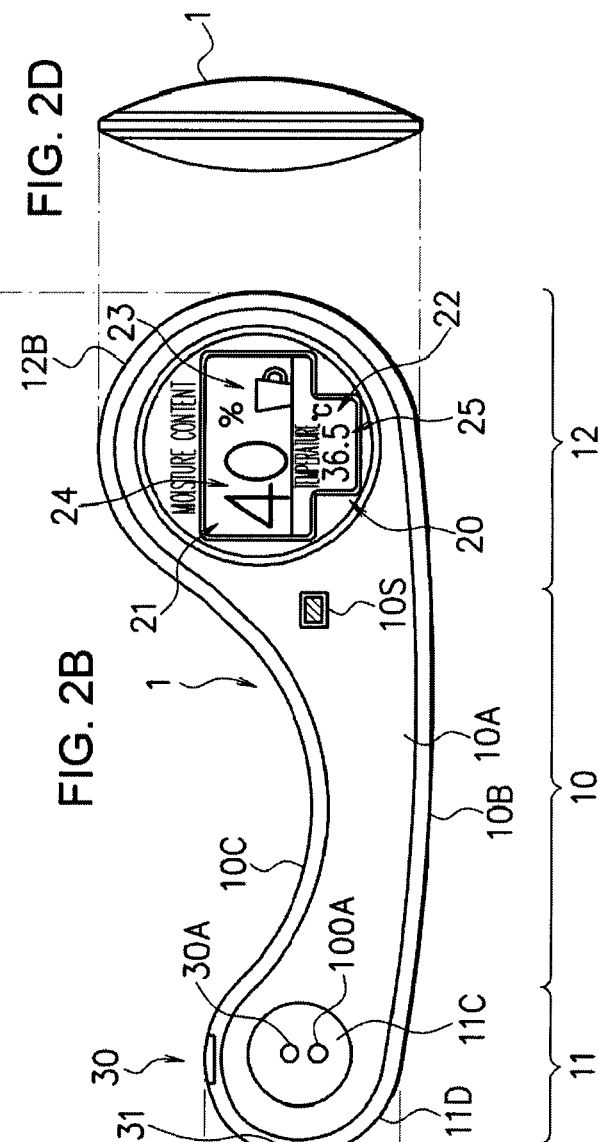
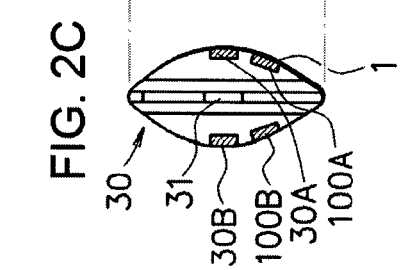

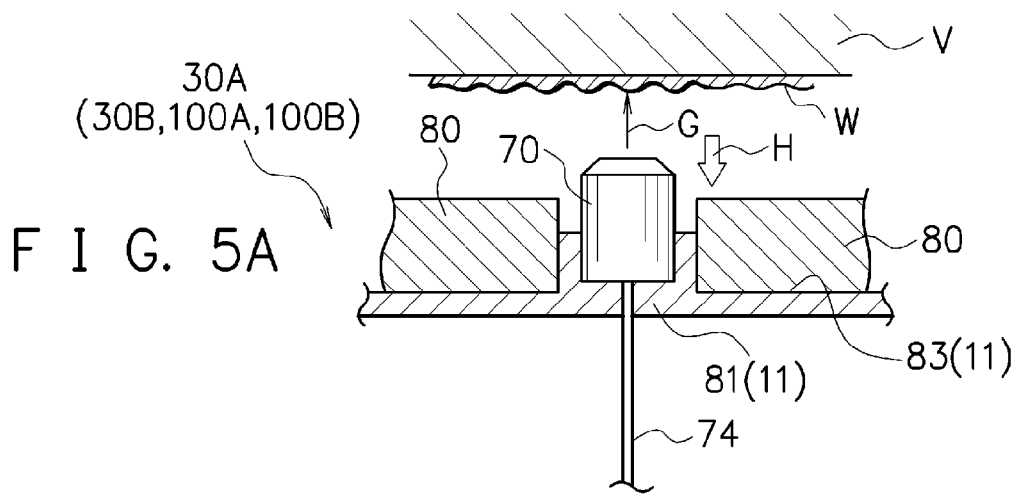
FIG. 5A
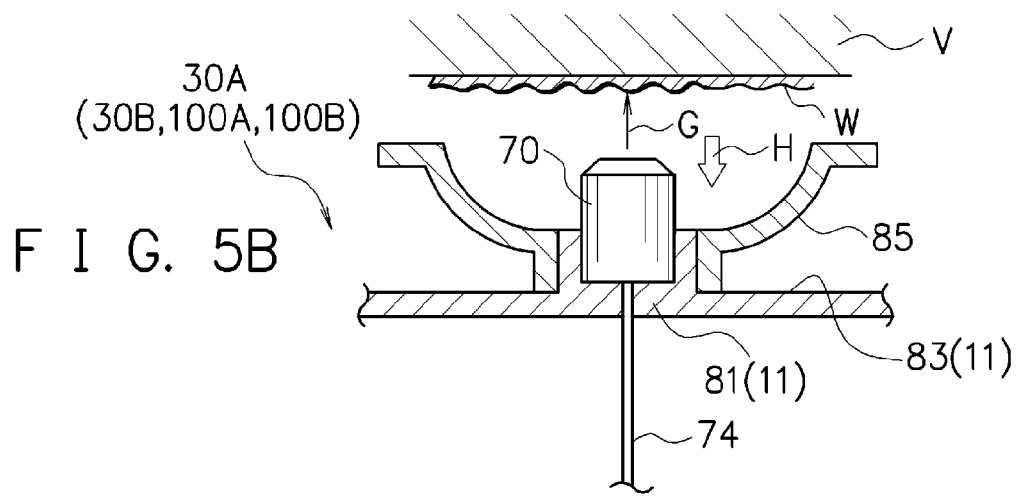
FIG. 5B
FIG. 6
|  |  | MOISTURE CONTENT | |
|---|---|---|---|
|  |  | LOW | NORMAL |
| TEMPERATURE | NORMAL | MINOR DEHYDRATION | HEALTHY |
|  | HIGH | HEAVY DEHYDRATION | ILLNESS OTHER THAN DEHYDRATION |

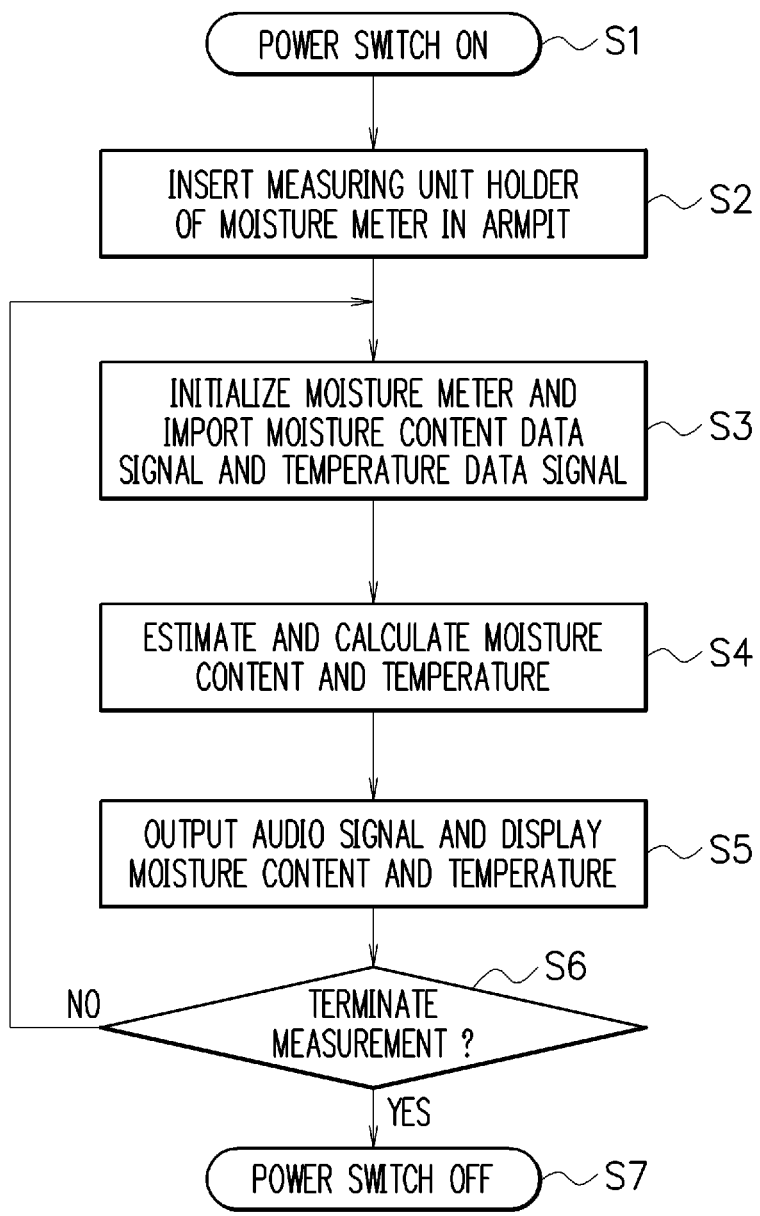

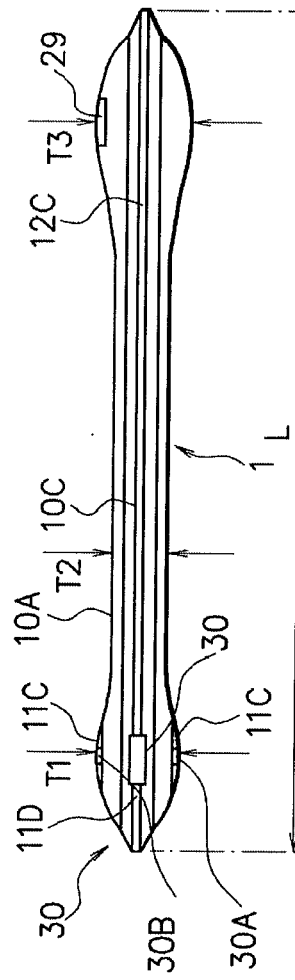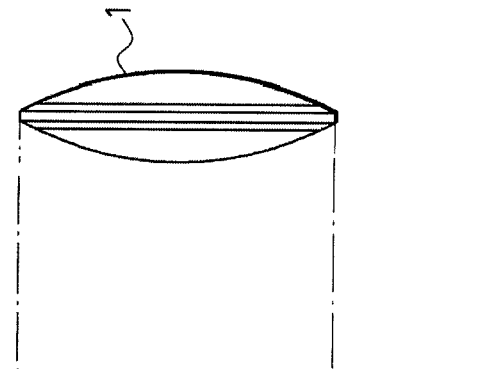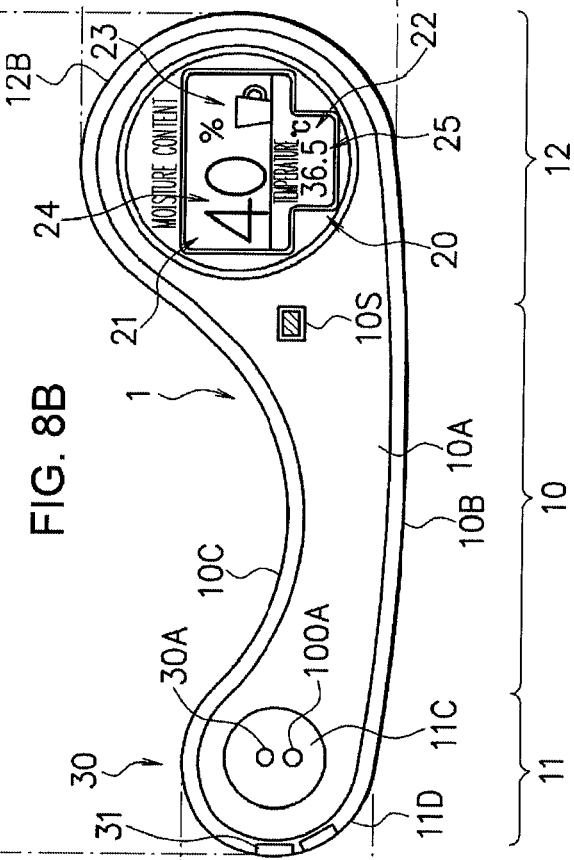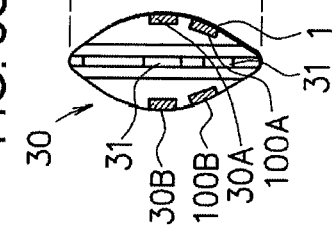

MOISTURE METER

TECHNICAL FIELD

The present invention relates to a moisture meter that is held in the armpit of a subject to measure a moisture content in a living body.

BACKGROUND ART

It is important to measure a moisture content in the living body of a subject. Dehydration in the living body is a pathological condition in which the moisture content in the living body decreases, and is a symptom that develops frequently in daily life, and in particular, develops more often when a subject is doing an exercise or the atmospheric temperature is high because a large amount of water is excreted from the body as a result of perspiration or a temperature rise. In particular, since in many case, older persons have a decreased ability to retain water in the living body, it is said that older persons are more likely to have dehydration than ordinary healthy persons.

In general, when a person gets older, the volume of muscles that store water decreases, the urinary volume increases due to a decrease in the kidney function, the ability to sense thirst in the mouth decreases due to dulled sensitivity, and the moisture content required for the cells decreases. When the dehydration is left without any treatment, the dehydration may cause and even develop into severe symptoms. Infants may also suffer from the same dehydration. Although the moisture content of infants generally large, the infants cannot appropriately appeal for the supply of water by themselves and may have dehydration since the persons who care the infants recognize it too late.

In general, it is said that a disorder in temperature regulation occurs when more than 2% of weight of moisture in the living body is lost. The disorder in temperature regulation causes such a vicious circle that it causes an increase in temperature, which in turn causes a reduction in the moisture content in the living body, and finally results in a pathological condition called a heat illness. Heat illnesses include heat cramps, heat exhaustion, heat strokes, which may sometimes cause organ disorder in the entire body. Thus, it is preferable to accurately detect dehydration to prevent such a danger that leads to heat illnesses.

As a device for detecting dehydration, an apparatus that measures a body impedance using such a device having handles to be held by both hands to calculate a moisture content from the measured impedance is known (see Patent Documents 1 to 3).

As another device for detecting dehydration, an oral moisture meter or the like that measures a moisture content in the mouth such as lingual mucosa, buccal mucosa or palate is known (see Patent Documents 4 to 6).

As a method for measuring moisture content in the skin, an in-vitro mass method, a Karl Fischer method, an in-vivo ATR spectroscopy, and a high-frequency impedance method and electrical conductivity method which are simpler in-vivo measurement methods are generally used.

CITATION LIST

Patent Literature

Patent Literature 1: Japanese Patent Application Laid-open No. H11-318845

Patent Literature 2: Japanese Patent Publication No. 3977983

Patent Literature 3: Japanese Patent Publication No. 3699640

Patent Literature 4: WO2004/028359

Patent Literature 5: Japanese Patent Application Laid-open No. 2001-170088

Patent Literature 6: Japanese Patent Application Laid-open No. 2005-287547

SUMMARY OF INVENTION

Technical Problem

However, the moisture meter that measures the body impedance using such a device having handles to be held by both hands to calculate the moisture content from the body impedance measures the impedance of the skin of the hand. Thus, the apparatus is likely to be influenced by the humidity of the skin, the volume of arm muscles, and the like and is not user-friendly because the apparatus is too tall for older persons or physically disabled persons so these persons have to stand up to get measurements.

It is generally known that the bioelectrical impedance value decreases as the temperature increases and the bioelectrical impedance value increases as the temperature decreases, that is, the bioelectrical impedance value (that is, the moisture content) changes as the temperature changes. However, since the conventional moisture meter calculates the body moisture content from the bioelectrical impedance value that is measured without taking the fact that the bioelectrical impedance value varies with the temperature into consideration, it is not possible to obtain an accurate body moisture content and to accurately detect dehydration. For example, when the body moisture content decreases and the temperature increases, the bioelectrical impedance value increases due to the decrease in the body moisture content whereas the bioelectrical impedance value decreases due to the increase in the temperature. Thus, the dehydration state may be not detected even if it is determined based on the body moisture content that is calculated from the bioelectrical impedance value. Thus, when measurement is performed according to the impedance method, although it is necessary to know the temperature of the subject, the impedance value is not corrected based on the measured temperature, or a warning that it is not possible to determine the accurate moisture content because the subject has a fever is not output.

In the oral moisture meter that measures a moisture content in the mouth such as lingual mucosa, buccal mucosa or palate, it is necessary to attach a replaceable cover for each subject to a portion that is directly inserted into the mouth in order to prevent contaminations between subjects. Thus, users may forget to replace and attach the cover, and the oral moisture meter is not user-friendly to older persons or physically disabled persons.

A dehydration state determining apparatus disclosed in Japanese Patent Publication No. 13977983 includes a temperature sensor that measure the temperature of the thumb, and the apparatus corrects a measured bioelectrical impedance based on the temperature and determines a dehydration state based on the corrected bioelectrical impedance value. Since the dehydration state is determined based on the bioelectrical impedance value with the temperature taken into consideration, the dehydration state can be determined more accurately, and the subject can accurately examine the dehydration state.

However, in this document, although the temperature is measured using the thumb, it is difficult to measure the temperature in the thumb, which is not a practical method.

In the medical field, dehydration is determined by several methods. For example, observations that indicate dehydration based on blood data include a high hematocrit level, a high sodium level, an urea nitrogen level of 25 mg/dL or more, a urea nitrogen/creatinine ratio of 25 or more, and an uric acid level of 7 mg/dl or more. However, this method requires collecting blood and may not be used at homes or the like.

As other determination methods, the dehydration can be determined based on indications such as a dryness state of the tongue and the mouth, a dryness state of the armpit, lack of the will to do something such as "feeling weak for some reason", or dulled consciousness such as "being unconscious and slow to respond". All these methods require intuition and experience that only medical workers can have, and ordinary persons cannot use such methods.

Therefore, an object of the present invention is to provide a moisture meter that can easily measure a moisture content of a subject and discover dehydration early and can be effectively used as means for assisting the subject in appropriately regulating moisture content.

Solution to Problem

A moisture meter according to the present invention is a moisture meter for measuring a moisture content of a subject, including an electrical moisture measuring unit that is held in an armpit of the subject so as to measure a moisture content of the subject, the impedance-type moisture measuring unit including a measurement current supply electrode portion and a voltage measurement electrode portion that make contact with a skin surface of the armpit.

According to this configuration, the moisture meter can measure the moisture content of the subject easily and can be effectively used as means for assisting the subject in appropriately regulating the moisture content.

The electrical moisture measuring unit in the present invention may be any one of an impedance-type moisture measuring unit and an electrostatic capacitance-type moisture measuring unit.

In general, it is known that sweat glands come in two types of apocrine glands and eccrine glands. In the case of human, the eccrine glands are distributed all over the body, whereas the apocrine glands are present in limited locations such as the armpit, the ear canal, the lower abdomen, and the vulva.

The reason for selecting the armpit as the location of the living body where the moisture content of the subject can be appropriately measured using the moisture meter and measuring the moisture content in the living body of the subject is because the moisture content measured in the armpit best reflects the moisture state of the entire living body of the subject due to the above reason.

It is generally known that the bioelectrical impedance value decreases as the temperature increases and the bioelectrical impedance value increases as the temperature decreases, that is, the bioelectrical impedance value (that is, the moisture content) changes as the temperature changes. However, since the conventional moisture meter calculates the body moisture content from the bioelectrical impedance value that is measured without taking the fact that the bioelectrical impedance value varies with the temperature into consideration, it is not possible to obtain an accurate body moisture content and to accurately detect dehydration.

For example, when the body moisture content decreases and the temperature increases, the bioelectrical impedance value increases due to the decrease in the body moisture content whereas the bioelectrical impedance value decreases due to the increase in the temperature. Thus, the dehydration state may be not detected even if it is determined based on the body moisture content that is calculated from the bioelectrical impedance value. Thus, when measurement is performed according to the impedance method, although it is necessary to know the temperature of the subject, the impedance value is not corrected based on the measured temperature, or a warning that it is not possible to determine the accurate moisture content because the subject has a fever is not output.

For the above reasons, preferably, the moisture meter includes a temperature measuring unit that is held in the armpit of the subject so as to measure temperature of the subject.

According to this configuration, by measuring the temperature of the subject simultaneously with measuring the moisture content of the subject in the armpit of the subject, the state of the subject can be determined using the correlations between the measured moisture content and temperature.

Preferably, the moisture meter includes a main body, a measuring unit holder that is disposed at one end of the main body and is sandwiched in the armpit while holding the impedance-type moisture measuring unit and the temperature measuring unit, and a display unit holder that is disposed at the other end of the main body so as to hold a display unit that displays the measured moisture content of the subject and the measured temperature of the subject.

According to this configuration, the main body has such a shape that the subject can easily hold or grip with the hand, the display unit holder can protrude to the front side from the armpit in a state where the measuring unit holder is sandwiched in the armpit, and the person who makes measurements can read the moisture content and temperature displayed on the display unit with the naked eyes.

Preferably, a plurality of the temperature measuring units is held on the measuring unit holder.

According to this configuration, it is possible to obtain the average of the measured temperature values using a plurality of temperature measuring units and to obtain more accurate moisture content and temperature.

Similarly, by using a plurality of moisture measuring units, it is possible to obtain the average of the measured moisture contents. When both the temperature measuring unit and the moisture measuring unit are provided, the time taken in measuring the temperature becomes longer than the time taken in measuring the moisture content, and a time difference may occur. By taking most of this time difference, the moisture content may be measured multiple times using the same moisture measuring unit and the measured values may be averaged. For example, the moisture content may be measured ten times whenever the temperature is measured once.

Preferably, each of the electrode portions of the impedance-type moisture measuring unit includes an electrode terminal for making direct contact with the skin surface of the armpit, and an elastically deformable member for pressing the electrode terminal against the skin surface of the armpit.

According to this configuration, when measuring the moisture content and temperature, the electrode terminal can be reliably brought into contact with the skin surface of the armpit.

Preferably, each of the electrode portions of the impedance-type moisture measuring unit includes an electrode terminal for making direct contact with the skin surface of the armpit, and a sticking member for making close contact with the skin surface of the armpit to press the electrode terminal against the skin surface of the armpit.

According to this configuration, when measuring the moisture content and temperature, the electrode terminal can be reliably brought into contact with the skin surface of the armpit.

A moisture meter according to the present invention is a moisture meter for measuring a moisture content of a subject, including: an electrostatic capacitance-type moisture measuring unit that is held in an armpit of the subject to measure a moisture content in the armpit in order to measure the moisture content of the subject, wherein the moisture measuring unit detects an electrostatic capacitance using a plurality of electrodes to measure the moisture content based on a variation in permittivity that changes with a moisture content ratio.

According to this configuration, it is possible to measure the moisture content in the armpit of the subject based on the electrostatic capacitance.

Advantageous Effects of Invention

The present invention can provide a moisture meter that can easily measure a moisture content of a subject and can be effectively used as means for assisting the subject in appropriately regulating moisture content.

BRIEF DESCRIPTION OF DRAWINGS

FIGS. 2A-2D are diagrams showing an appearance of the moisture meter shown in FIG. 1 from various directions. FIG. 2A is a top view of the moisture meter, FIG. 2B is a front view of the moisture meter, FIG. 2C is a left side view of the moisture meter, and FIG. 2D is a right side view of the moisture meter.

FIG. 5 is a diagram showing further examples of the structure of the impedance-type moisture measuring unit.

FIG. 6 is a diagram showing examples of patient symptoms based on correlations between a moisture content in the living body of a subject M and the temperature of the living body of the subject M.

FIG. 7 is a flowchart showing an example of a moisture content detecting operation of the moisture meter according to the present invention.

FIGS. 8A-8D are diagrams showing an appearance of another embodiment of the present invention from various directions. FIG. 8A is a top view of the moisture meter, FIG. 8B is a front view of the moisture meter, FIG. 8C is a left side view of the moisture meter, and FIG. 8D is a right side view of the moisture meter.

DESCRIPTION OF EMBODIMENTS

Hereinafter, preferred embodiments of the present invention will be described with reference to the drawings.

The embodiments described below are specific preferred examples of the present invention, and various limitations that are technically preferable are added. However, the scope of the present invention is not limited to these embodiments unless there is a particular statement that restricts the present invention.

Figure 1:
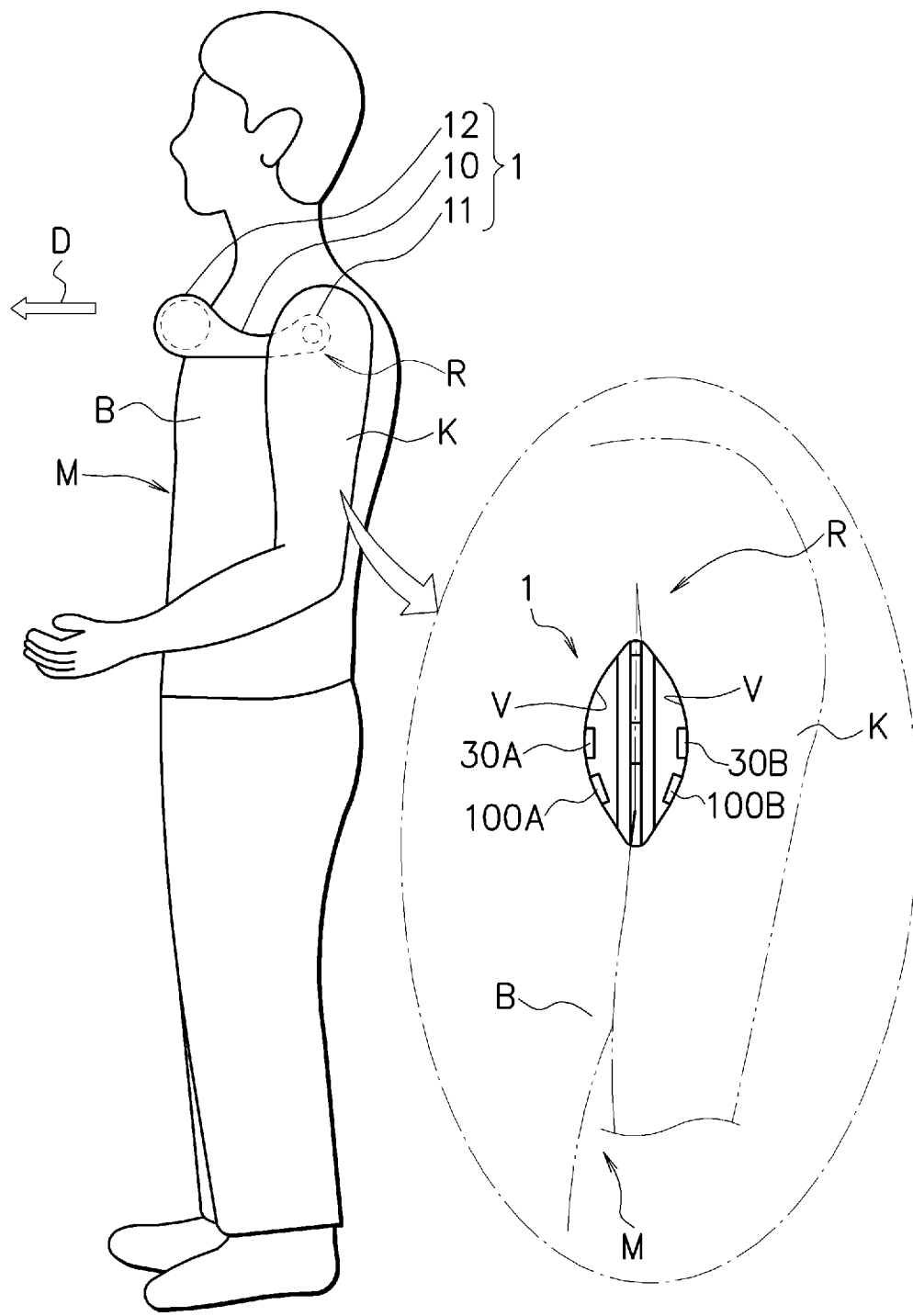
FIG. 1 is a diagram showing a state where a subject uses an embodiment of a moisture meter according to the present invention.

FIG. 1 is a diagram showing a state where a subject uses a preferred embodiment of a moisture meter according to the present invention. FIGS. 2A to 2D are diagrams showing an example of an external structure of the moisture meter shown in FIG. 1.

FIG. 2B shows a front part of the moisture meter 1, FIG. 2A shows an upper part of the moisture meter 1, FIG. 2C shows a side part of the moisture meter 1 shown in FIG. 2B as seen from the left side of the figure, and FIG. 2D shows a side part of the moisture meter 1 shown in the FIG. 2B as seen from the right side of the figure. All references below to "FIG. 2", collectively refer to FIG. 2A through FIG. 2D.

The moisture meter 1 shown in FIGS. 1 and 2 may be an electronic moisture meter or an armpit-type electronic moisture meter, and the moisture meter 1 is a compact and portable moisture meter. As shown in FIG. 2, the moisture meter 1 roughly includes a main body 10, a measuring unit holder 11, and a display unit holder 12. A total weight of the moisture meter 1 is as light as approximately 20 grams, for example.

The main body 10, the measuring unit holder 11, and the display unit holder 12 are made from plastics, for example, and one end of the main body 10 is formed to be continuous with the measuring unit holder 11, and the other end of the main body 10 is formed to be continuous with the display unit holder 12.

The main body 10 is formed in such a shape that a subject M or the person who makes measurements can easily hold or grip. For example, the main body 10 includes a first curved portion 10B that is smoothly curved outward and a second curved portion 10C that is greatly curved inward, and the second curved portion 10C is more curved than the first curved portion 10B.

The reason why the main body 10 is formed in such a characteristic shape is to allow the subject M or the person who makes measurements to hold or grip the main body 10 with the hand to insert the measuring unit holder 11 of the moisture meter 1 in an armpit R so that the measuring unit holder 11 can be reliably held. The reason for selecting the armpit R as the location of the living body where the moisture content of the subject M can be appropriately measured using the moisture meter 1 and measuring the moisture content in the living body of the subject M is as follows. That is, the reason why the moisture content in the armpit R is measured is because the moisture content reflects a moisture state of the entire living body of the subject M. For example, even if the subject is old and thin, the measuring unit holder 11 of the moisture meter 1 can be reliably inserted and held in the armpit R between the body and the upper arm. Further, even if the subject is an infant, the measuring unit holder 11 can be reliably inserted and held in the armpit R.

The moisture meter 1 shown in FIG. 2 may have the following dimensions, for example. The main body 10 has a total length L of about 110 mm for large size (for adults), approximately 110 mm for medium size, and approximately 90 mm for small size (for infants). The moisture meter 1 generally has a flat shape except for part of the measuring unit holder 11 and the display unit holder 12.

The thickness T2 of a central portion 10A of the main body 10 is approximately 7 mm, the largest thickness T1 of the measuring unit holder 11 is approximately 9 mm, and the largest thickness T3 near the display unit holder 12 is approximately 14 mm.

However, these dimensions of the moisture meter 1 are not limited to the above examples but can be selected optionally.

As shown in FIG. 2, the measuring unit holder 11 of the moisture meter 1 includes a circular peripheral portion 11D, one convex portion 11C, and the other convex portion 11C. When the measuring unit holder 11 is inserted in the armpit R of the subject M shown in FIG. 1 using the two convex portions 11C and held by being pressed by an upper arm K, the moisture content in the living body of the subject M and the temperature thereof can be measured stably. One convex portion 11C is formed on the front side of the measuring unit holder 11, and the other convex portion 11C is formed on the rear side of the measuring unit holder 11.

In this manner, in a state where the measuring unit holder 11 of the moisture meter 1 is held in the armpit R, by bringing the main body 10 into close contact with a side portion of an upper body B of the subject, the moisture meter 1 can be more reliably held closer to the upper body B.

For example, as shown in FIG. 1, when the moisture meter is used, the display unit holder 12 can be held approximately horizontally so as to face the front D of the subject M. The distance between the measuring unit holder 11 and the display unit holder 12, that is the length of the main body 10 is set such that, when the subject M inserts the measuring unit holder 11 in the armpit R, a display unit 20 in the display unit holder 12 is positioned at a position outside the armpit R (the position where the display unit 20 is not pinched between the body portion of the subject M and the upper arm K).

The display unit holder 12 shown in FIG. 2 includes a circular peripheral portion 12B, and the display unit 20 having a circular shape, for example, is held on the front side of the display unit holder 12. A liquid crystal display device, an organic EL device, and the like can be used as the display unit 20, for example. A speaker 29 as a sound generator is disposed on the back side of the display unit holder 12. In this manner, since the display unit 20 is disposed on the front side of the display unit holder 12, and the speaker 29 is disposed on the back side, the display unit and the speaker 29 are not positioned in the armpit R. Thus, the subject M can easily check the moisture content and the temperature displayed on the display unit 20 and listen to sound guidance or the like generated from the speaker 29.

As shown in FIG. 2, the display unit 20 includes a screen (hereinafter referred to as a moisture content display screen) 21 for displaying the moisture content (%) in the living body of the subject and a screen (hereinafter referred to as a temperature display screen) 22 for displaying the temperature (° C.). The moisture content display screen 21 includes a moisture content suggestive mark 23 and can display the moisture content using a relatively large digital indication 24 for example as 40%. In the example of FIG. 2, the temperature display screen 22 can display the temperature of the subject using a temperature digital indication 25 for temperature in a smaller size than the moisture content digital indication 24. However, the configuration of the display unit 20 is not limited to the example shown in FIG. 2, and the moisture content digital indication 24 and the temperature digital indication 25 may have the same size.

As shown in FIG. 2, the measuring unit holder 11 of the moisture meter 1 holds a so-called bioelectrical impedance-type (hereinafter simply referred to as impedance-type) moisture measuring unit 30 and a temperature measuring unit 31. Preferably, anti-slip means is arranged on the surface of the measuring unit holder 11 by forming an uneven surface according to dimple processing or the like, for example. According to this configuration, when the subject M inserts the measuring unit holder 11 in the armpit R, it is possible to provide such a shape that the measuring unit holder 11 of the moisture meter 1 is reliably and stably sandwiched and to decrease thermal capacity to attain a thermal equilibrium state early.

The impedance-type moisture measuring unit 30 shown in FIG. 2 is a portion that measures the moisture content in the living body of the subject M using bioelectrical impedance of the armpit R of the subject shown in FIG. 1.

As shown in FIG. 2, preferably, a first measurement current supply electrode portion 30A and a first voltage measurement electrode portion 100A are disposed on one convex portion 11C of the measuring unit holder 11, and a second measurement current supply electrode portion 30B and a second voltage measurement electrode portion 100B are disposed on the other convex portion 11C of the measuring unit holder 11.

For example, as shown in FIG. 1, when the impedance-type moisture measuring unit 30 is inserted in the armpit R of the subject, the first measurement current supply electrode portion 30A and the first voltage measurement electrode portion 100A come into close contact with a skin surface V closer to the side surface of the upper body B, and the second measurement current supply electrode portion 30B and the second voltage measurement electrode portion 100B come into close contact with the skin surface V closer to the inner side of the upper arm K.

In this manner, as shown in FIG. 1, since the first and second measurement current supply electrode portions 30A and 30B and the first and second voltage measurement electrode portions 100A and 100B can be reliably in direct contact with the skin surface V of the armpit R, the moisture content of the subject M is measured. An example of the structure of the first and second measurement current supply electrode portions 30A and 30B and the first and second voltage measurement electrode portions 100A and 100B will be described with reference to FIGS. 4 and 5.

The temperature measuring unit 31 of FIG. 2 is a portion that measures the temperature of the living body of the subject M in the armpit R of the subject shown in FIG. 1, and preferably, is disposed along the peripheral portion 11D of the measuring unit holder 11 so as to be exposed.

Returning to FIG. 2, the temperature measuring unit is a portion that measures the temperature of the living body in the armpit R of the subject, and preferably, is disposed along the peripheral portion 11D of the measuring unit holder 11 so as to be exposed. In this manner, the temperature measuring unit 31 can be reliably in direct contact with the skin surface of the armpit R.

The temperature measuring unit 31 is configured to detect the temperature by making contact with the armpit R of the subject M shown in FIG. 1, and for example, a temperature measuring unit having a thermistor or a thermocouple may be used as the temperature measuring unit 31. For example, a temperature signal detected by the thermistor is converted into a digital signal and is output. The thermistor is liquid-tightly protected by a metal cap made from stainless steel, for example.

Figure 3:
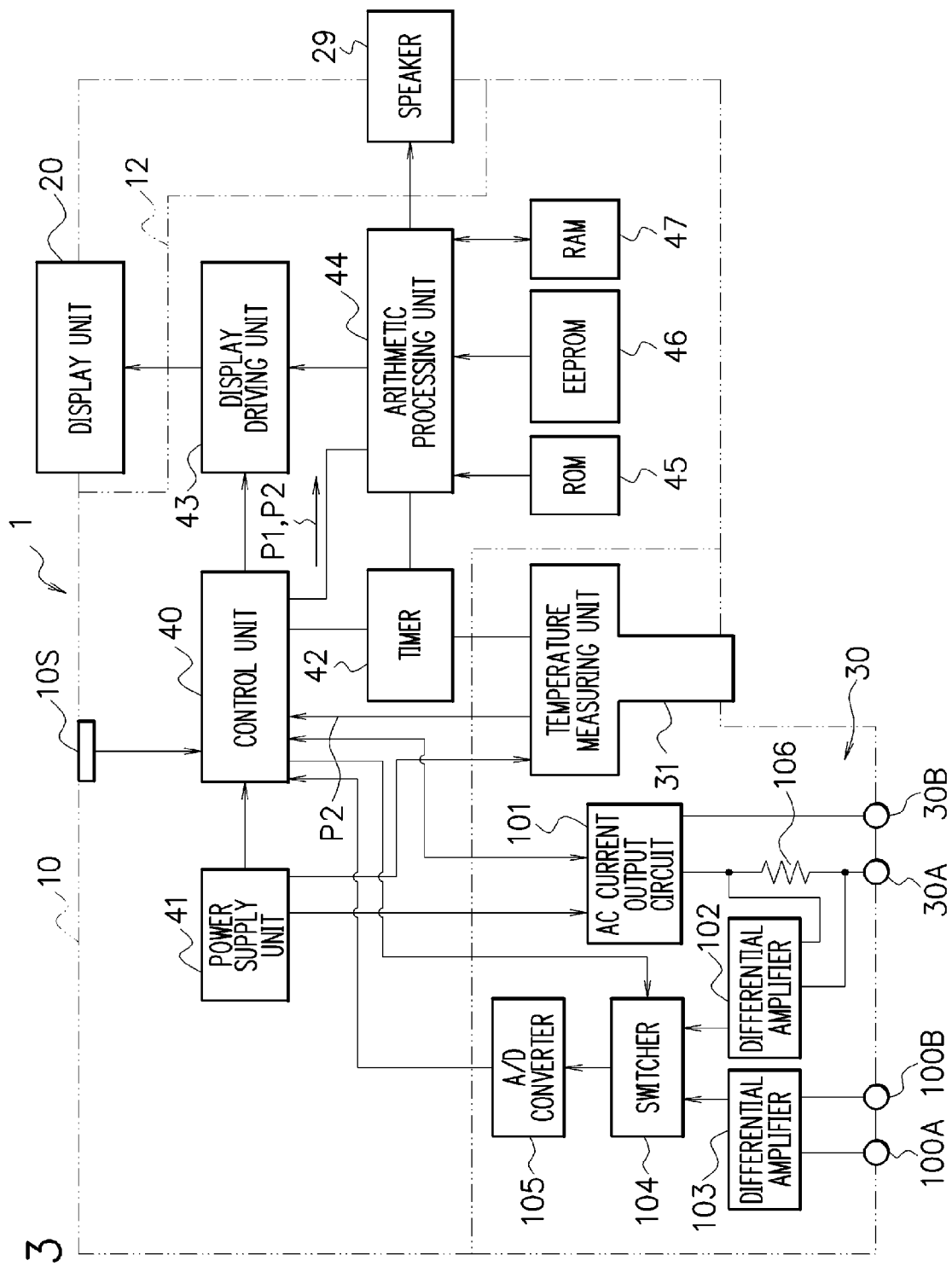
FIG. 3 is a block diagram showing a functional configuration of the moisture meter shown in FIG. 2.

FIG. 3 is a block diagram showing a functional configuration of the moisture meter 1 shown in FIG. 2.

In the block diagram of the moisture meter 1 shown in FIG. 3, the main body 10 includes a control unit 40, a power supply unit 41, a timer 42, a display driving unit 43, an arithmetic processing unit 44, a read only memory (ROM) 45, an electrically erasable PROM (EEPROM) 46, and a random access memory (RAM) 47. The impedance-type moisture measuring unit 30 and the temperature measuring unit 31 are disposed in the measuring unit holder 11, and the display unit 20 and the speaker 29 are disposed in the display unit holder 12.

The power supply unit 41 of FIG. 3 is a rechargeable secondary battery or a primary battery and supplies power to the control unit 40, the impedance-type moisture measuring unit 30, and the temperature measuring unit 31. The control unit 40 is electrically connected to a power switch 10S, the impedance-type moisture measuring unit 30, the temperature measuring unit 31, the timer 42, the display driving unit 43, and the arithmetic processing unit 44. The control unit 40 controls the entire operation of the moisture meter 1.

The display unit 20 of FIG. 3 is electrically connected to the display driving unit 43, and the display driving unit 43 displays the moisture content suggestive mark 23 such as a cup, the moisture content digital indication 24, and the temperature digital indication 25 as shown in FIG. 2 on the display unit 20 according to a command from the control unit 40.

The arithmetic processing unit 44 of FIG. 3 is electrically connected to the speaker 29, the ROM 45, the EEPROM 46, and the RAM 47. The ROM 45 stores a program for estimating and calculating the moisture content and temperature of the subject based on a change over time in moisture content data and temperature data, calculated from the moisture content data obtained from an impedance value measured by the impedance-type moisture measuring unit 30 and the temperature data measured by the temperature measuring unit 31 based on the time measured by the timer 42. The EEPROM 46 stores predetermined audio data. The RAM 47 can store the calculated moisture content data and temperature data in association with time.

As described above, it is generally known that the bioelectrical impedance value decreases as the temperature increases and the bioelectrical impedance value increases as the temperature decreases, that is, the bioelectrical impedance value (that is, the moisture content) changes as the temperature changes. Thus, it is possible to correct the bioelectrical impedance value using the measured temperature data.

The arithmetic processing unit 44 estimates and calculates the moisture content and temperature of the subject according to the program stored in the ROM 45 and outputs audio data to the speaker 29.

Next, the impedance-type moisture measuring unit 30 will be described.

In measurement of the moisture content based on the bioelectrical impedance, of the moisture meter 1 according to the embodiment of the present invention, the following can be mentioned. A cellular tissue of a human body is made up of a number of cells, and each cell is present in an environment filled with extracellular fluid. When a current flows into such a cellular tissue, a low-frequency AC current mainly flows into an extracellular fluid region, and a high-frequency AC current flows into an extracellular fluid region and cells.

When a current flows into a cellular tissue in this manner, the electrical impedance value of an extracellular fluid region is composed of a resistance component only, and the electrical impedance value of cells is composed of a series connection of a capacitance component of a cellular membrane and a resistance component of intracellular fluid.

The electrical properties of the living body (body) of the subject M change greatly depending on the type of tissues or organs. The electrical properties of the entire body including these tissues and organs can be represented by the bioelectrical impedance.

The bioelectrical impedance value is measured by flowing a very small current between a plurality of electrodes attached to the body surface of the subject. From the bioelectrical impedance value obtained in this manner, a body fat percentage, a body fat mass, a lean body mass, a body moisture content, and the like of the subject can be estimated (see Non-Patent Document 1: "Impedance-ho ni Yoru Taishi no Suibun Bunpu to Sono Ouyo (Estimation of Fluid Distribution by Impedance Method)", Medical Electronics and Biological Engineering, Vol. 23, No. 6, 1985).

As for the moisture content in the living body, a method of estimating the same by calculating an extracellular fluid resistance and an intracellular fluid resistance is known. As for measurement of the moisture content, a method of estimating the same by calculating an extracellular fluid resistance and an intracellular fluid resistance based on the fact that the bioelectrical impedance value has a small value when the moisture content in the living body is large whereas the bioelectrical impedance value has a large value when the moisture content in the living body is small is known.

The impedance-type moisture measuring unit 30 shown in FIG. 3 is a device that applies an AC current to the living body of the subject M to measure the bioelectrical impedance value.

The impedance-type moisture measuring unit 30 includes the first and second measurement current supply electrode portions 30A and 30B, the first and second voltage measurement electrode portions 100A and 100B, an AC current output circuit 101, two differential amplifiers 102 and 103, a switcher 104, an A/D converter 105, and a reference resistor 106.

The first and second measurement current supply electrode portions 30A and 30B and the first and second voltage measurement electrode portions 100A and 100B are provided in the measuring unit holder 11 shown in FIG. 2, for example so as to be exposed to the outside. Due to this, these four electrode portions 30A, 30B, 100A, and 100B can be brought into direct contact with the skin surface of the armpit R of the subject M shown in FIG. 1.

The AC current output circuit 101 of FIG. 3 is electrically connected to the control unit 40 and the first and second measurement current supply electrode portions 30A and 30B, and the reference resistor 106 is disposed between the AC current output circuit 101 and the first measurement current supply electrode portion 30A. The differential amplifier 102 is connected to both ends of the reference resistor 106. The other differential amplifier 103 is electrically connected to the first and second voltage measurement electrode portions 100A and 100B. The two differential amplifiers 102 and 103 are electrically connected to the control unit 49 via the switcher 104 and the A/D converter 105.

In FIG. 3, when the control unit 40 supplies a predetermined living body application signal to the AC current output circuit 101, the AC current output circuit 101 supplies an AC measurement current to the first and second measurement current supply electrode portions 30A and 30B via the reference resistor 106. One differential amplifier 102 detects a potential difference between both ends of the reference resistor 106. The other differential amplifier 103 detects a potential difference between the voltage measurement electrode portions 100A and 100B. The switcher 104 selects any one of the potential difference outputs from the differential amplifiers 102 and 103 and delivers the selected potential difference output to the A/D converter 105. The A/D converter 105 performs A/D conversion on the potential difference outputs of the differential amplifiers 102 and 103 to obtain digital signals and supplies the digital signals to the control unit 40.

Next, an example of the structure of the first and second measurement current supply electrode portions 30A and 30B and the first and second voltage measurement electrode portions 100A and 100B of the impedance-type moisture measuring unit 30 will be described with reference to FIGS. 4 and 5.

The first and second measurement current supply electrode portions 30A and 30B may employ the same structure as the first and second voltage measurement electrode portions 100A and 100B. FIGS. 4 and 5 show the skin surface V and the moisture W on the skin surface V.

Figure 4A:
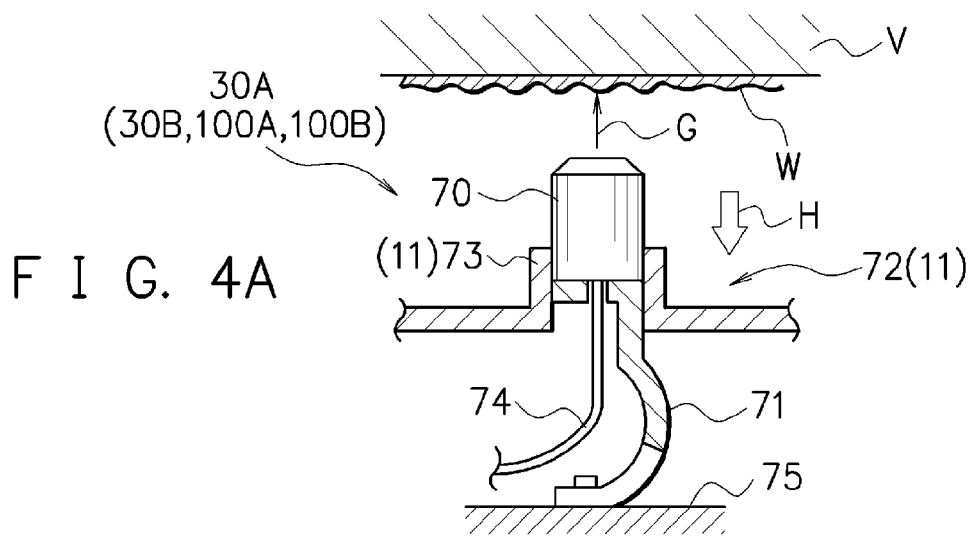
FIG. 4 is a diagram showing examples of the structure of an electrode portion of an impedance-type moisture measuring unit.

The structure of the first and second measurement current supply electrode portions 30A and 30B and the first and second voltage measurement electrode portions 100A and 100B shown in FIG. 4(A) includes an electrode terminal 70, a semicircular plate-shaped elastically deformable member 71, and an electrode terminal guiding portion 72. The electrode terminal 70 having conductivity is connected to a wire 74, and the elastically deformable member 71 has one end fixed to a lower portion of the electrode terminal 70 and the other end connected to a fixing portion 75 in the measuring unit holder 11 shown in FIG. 2. The electrode terminal guiding portion 72 has a cylindrical portion 73, and the lower portion of the electrode terminal 70 is inserted in the cylindrical portion 73. Due to this, when the tip end of the electrode terminal is pressed against the skin surface V in the direction indicated by arrow G, the electrode terminal 70 is pushed in the direction indicated by arrow H while resisting against the repulsive force of the elastically deformable member 71. Thus, the tip end of the electrode terminal 70 can be reliably in contact with the skin surface V so as not to be separated.

Figure 4B:
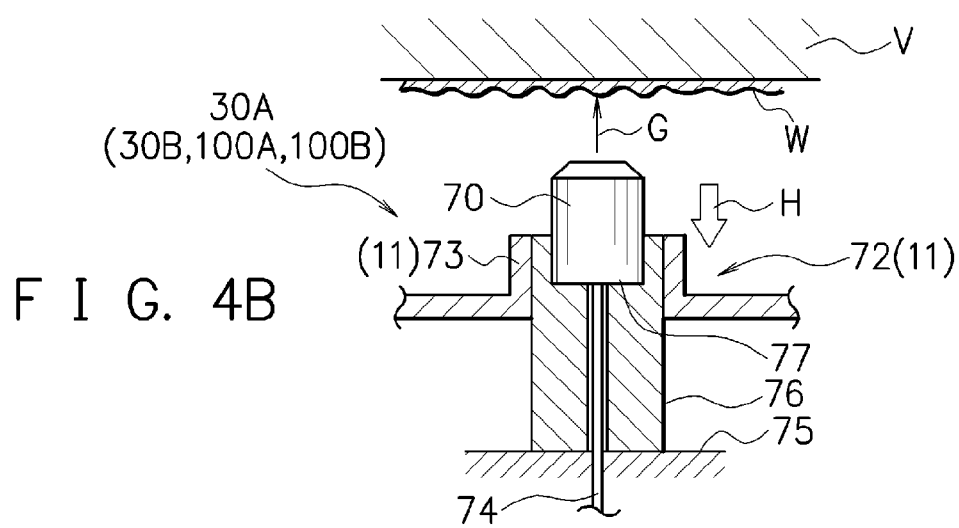

The structure of the first and second measurement current supply electrode portions 30A and 30B and the first and second voltage measurement electrode portions 100A and 100B shown in FIG. 4(B) includes an electrode terminal 70, an elastically deformable member 76 formed of a columnar cushion body, and an electrode terminal guiding portion 72. The electrode terminal 70 having conductivity is connected to a wire 74, a lower portion of the electrode terminal 70 is fitted and fixed to a concave portion 77 at the upper end of the elastically deformable member 76, and the other end of the elastically deformable member 76 is fixed to a fixing portion in the measuring unit holder 11 shown in FIG. 2. The electrode terminal guiding portion 72 has a cylindrical portion 73, and the upper end of the elastically deformable member 76 is inserted in the cylindrical portion 73. Due to this, when the tip end of the electrode terminal 70 is pressed against the skin surface V in the direction indicated by arrow G, the electrode terminal 70 is pushed in the direction indicated by arrow H while resisting against the repulsive force of the elastically deformable member 76. Thus, the tip end of the electrode terminal 70 can be reliably in contact with the skin surface V so as not to be separated.

Figure 4C:
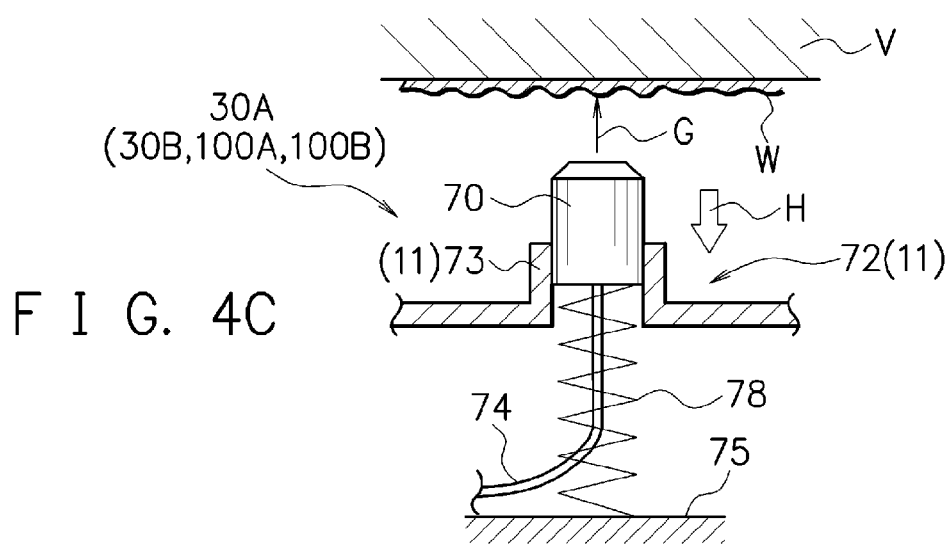

The structure of the first and second measurement current supply electrode portions 30A and 30B and the first and second voltage measurement electrode portions 100A and 100B shown in FIG. 4(C) includes an electrode terminal 70, an elastically deformable member 78 having a coil spring shape, and an electrode terminal guiding portion 72. The electrode terminal 70 having conductivity is connected to a wire 74, and the elastically deformable member 78 has one end fixed to a lower portion of the electrode terminal 70 and the other end fixed to a fixing portion 75 in the measuring unit holder 11 shown in FIG. 2. The electrode terminal guiding portion 72 has a cylindrical portion 73, and the lower portion of the electrode terminal 70 is inserted in the cylindrical portion 73. Due to this, when the tip end of the electrode terminal is pressed against the skin surface V in the direction indicated by arrow G, the electrode terminal 70 is pushed in the direction indicated by arrow H while resisting against the repulsive force of the elastically deformable member 78. Thus, the tip end of the electrode terminal 70 can be reliably in contact with the skin surface V so as not to be separated.

The structure of the first and second measurement current supply electrode portions 30A and 30B and the first and second voltage measurement electrode portions 100A and 100B shown in FIG. 4(D) includes an electrode terminal 70, an adhesive member 80, and an electrode terminal fixing portion 81. The electrode terminal 70 having conductivity is connected to a wire 74, and a lower portion of the electrode terminal 70 is fitted and fixed to the electrode terminal fixing portion 81 having a cylindrical shape. The adhesive member 80 is a sticking member for pressing the electrode terminal 70 against the skin surface of the armpit R and is attached and fixed to a surface portion 83 of the measuring unit holder 11 shown in FIG. 2. Due to this, when the tip end of the electrode terminal 70 is pressed against the skin surface V in the direction indicated by arrow G, the adhesive member 80 is attached to the skin surface V. Thus, the tip end of the electrode terminal 70 can be reliably in contact with the skin surface V so as not to be separated in a state of being pushed in the direction indicated by arrow H.

The structure of the first and second measurement current supply electrode portions 30A and 30B and the first and second voltage measurement electrode portions 100A and 100B shown in FIG. 4(E) includes an electrode terminal 70, a sucking disk 85, and an electrode terminal fixing portion 81. The electrode terminal 70 having conductivity is connected to a wire 74, and a lower portion of the electrode terminal 70 is fitted and fixed to the electrode terminal fixing portion 81 having a cylindrical shape. The sucking disk 85 is a sticking member for pressing the electrode terminal 70 against the skin surface of the armpit R and is attached and fixed to a surface portion 83 of the measuring unit holder 11 shown in FIG. 2. Due to this, when the tip end of the electrode terminal 70 is pressed against the skin surface V in the direction indicated by arrow G, the sucking disk 85 is attached to the skin surface V. Thus, the tip end of the electrode terminal 70 can be reliably in contact with the skin surface V so as not to be separated in a state of being pushed in the direction indicated by arrow H.

It is known that a continued dehydration state may develop into various symptoms. Among them, a heat illness is the most dangerous problem. As a method of discovering such a symptom or a method of determining the severity of the symptom, it is preferable to measure the temperature together with the moisture content. The symptoms of a subject can be determined from the correlations between the moisture content in the living body of the subject M and the temperature of the living body of the subject M, for example, which will be described with reference to FIG. 6.

The correlations between the moisture content in the living body of the subject M and the temperature of the living body of the subject M shown in FIG. 6 are stored in the ROM 45 of FIG. 3, for example.

In FIG. 6, it can be determined that when the moisture content is low and the temperature is normal, the subject has minor dehydration, whereas when the moisture content is normal and the temperature is normal, the subject is healthy. In contrast, it can be determined that when the moisture content is low and the temperature is high, the subject has severe dehydration, whereas when the moisture content is normal and the temperature is high, the subject has an illness other than dehydration such as a cold.

In this manner, since the health, minor or severe dehydration, cold-like symptoms of a subject can be determined from the moisture content and temperature of the living body of the subject, it is important for the moisture meter 1 according to the embodiment of the present invention to measure the moisture content and temperature in the armpit R. The determination results on the symptoms of the subject may be displayed on the display unit 20 shown in FIG. 2.

FIG. 7 is a flowchart showing an example of the operation of the moisture meter 1 detecting the moisture content and temperature of the subject M.

Next, an example of the operation of the moisture meter 1 shown in FIGS. 1 and 2, detecting the moisture content and temperature of the subject M will be described with reference to FIG. 7.

In step S1 of FIG. 7, the subject turns ON the power switch 10S shown in FIG. 3, and when the ON signal is delivered to the control unit 40, the moisture meter 1 enters a measurement ready state. In step S2, as shown in FIG. 1, the subject M inserts the measuring unit holder 11 of the moisture meter 1 in the armpit R using the two convex portions 11C shown in FIG. 2.

In a state where the measuring unit holder 11 of the moisture meter 1 is held in the armpit R, by bringing the main body 10 into closer contact with the side portion of the upper body B of the subject, the moisture meter 1 can be more reliably held on the upper body B of the subject. For example, the display unit holder 12 can be positioned approximately horizontally so as to face the front D of the subject M.

When the distance between the measuring unit holder 11 and the display unit holder 12 is set such that, when the subject M inserts the measuring unit holder 11 in the armpit R, the display unit 20 is positioned at a position outside the armpit R (the position where the display unit 20 is not pinched between the body portion and the upper arm). Thus, the subject M can easily read the moisture content digital indication 24 and the temperature digital indication 25 on the display unit 20 of the display unit holder 12. Further, the subject M can listen to the sound guidance generated from the speaker 29.

In step S3 of FIG. 7, when the measuring unit holder 11 of the moisture meter 1 is held in the armpit R, the arithmetic processing unit 44 initializes the moisture meter 1 and imports moisture content data signals P1 measured by the moisture measuring unit 30 and temperature data signals P2 measured by the temperature measuring unit 31 at predetermined sampling points in time based on a timing signal from the timer 42.

In this manner, when the moisture content data signals P1 are obtained from the moisture measuring unit 30, an AC current is applied from the AC current output circuit 101 to the subject M via the first and second measurement current supply electrode portions 30A and 30B that are in contact with the armpit R of the subject M as shown in FIG. 1. Moreover, a potential difference between two points of the armpit R of the subject is detected by the first and second voltage measurement electrode portions 100A and 100B that are in contact with the armpit R of the subject. The potential difference is supplied to the other differential amplifier 103, and the other differential amplifier 103 outputs a potential difference signal corresponding to the potential difference between two points of the subject M toward the switcher 104.

One differential amplifier 102 outputs a potential difference signal corresponding to the potential difference across the reference resistor 106 toward the switcher 104. When the control unit 40 switches the switcher 104, the potential difference signal from the differential amplifier 102 and the potential difference signal from the differential amplifier 103 are converted into digital signals by the A/D converter 105 and supplied to the control unit 40. The control unit 40 calculates a bioelectrical impedance value based on the digital signals. The control unit 40 calculates the moisture content data P1 from the obtained bioelectrical impedance value. The moisture content data P1 is delivered from the control unit 40 to the arithmetic processing unit 44.

In step S4, the arithmetic processing unit 44 can estimate and calculate the moisture content and temperature of the subject M based on a change over time of the moisture content data and the temperature data of the subject, obtained from the moisture content data P1 and the temperature data P2 measured by the temperature measuring unit 31.

In step S5 of FIG. 7, the calculated values of the moisture content and temperature of the subject M can be output from the speaker 29 of FIG. 3 as audio guidance, and the relatively large digital indication 24 and the temperature digital indication 25 can be displayed on the moisture content display screen 21 and the temperature display screen 22 of the display unit 20 shown in FIGS. 3 and 2, respectively.

In step S6, when the subject M terminates the measurement using the moisture meter 1, the power switch 10S of FIG. 3 is turned off. However, when the subject M does not terminate the measurement, the flow returns to step S3, and the processes of steps S3 to S6 are repeated.

The moisture meter 1 according to the embodiment of the present invention has a structure that the moisture content of the subject M can be measured in the armpit R where the moisture content can be measured appropriately. From the bioelectrical impedance value measured by the first and second measurement current supply electrode portions 30A and 30B and the first and second voltage measurement electrode portions 100A and 100B of the impedance-type moisture measuring unit 30, the arithmetic processing unit 44 can estimate and calculate the moisture content and temperature of the subject based on a change over time in the moisture content data and temperature data of the subject, obtained from the moisture content data P1 and the temperature data P2 measured by the temperature measuring unit 31. As a result, the moisture meter 1 can be effectively used as means for assisting in regulating an appropriate moisture content of infants and older persons, who have difficulty in drinking water appropriately when feeling thirsty, or of normal persons, who are exercising vigorously, as well as assisting in regulating a moisture content that is extremely vital to maintaining health in daily life.

The reason for selecting the armpit R as the location of the living body where the moisture content of the subject M can be appropriately measured and measuring the moisture content in the armpit R is because the moisture content in the armpit R reflects the moisture state of the entire living body of the subject M. In general, the skins of older persons are easily to dry, and the degree thereof varies greatly from person to person. Among the skins, the armpit R is less influenced from the outside as compared to other locations and incurs a small variation in measurement and is thus suitable for measurement. Even if the subject is old and thin, the measuring unit holder 11 of the moisture meter 1 can be reliably inserted and held in the armpit R between the body and the upper arm. Further, even if the subject is an infant, the measuring unit holder 11 can be reliably inserted and held in the armpit R. Furthermore, since the moisture measuring unit 30 has such a structure that it secures the central portion of the armpit R and thus provides higher measurement accuracy.

The moisture meter 1 according to the embodiment of the present invention preferably has such a structure that it can also measure the temperature of the armpit R simultaneously with measuring appropriately the moisture content of the subject M in this manner. Due to this, as shown in FIG. 5, health workers or caregivers can measure the moisture content of the subject M more easily since they only need to hold the measuring unit holder 11 of the moisture meter 1 in the armpit R of the subject M than measuring the moisture content from the mouth or the like.

As shown in FIG. 2, from the correlations between the moisture content in the living body of the subject M and the temperature of the living body of the subject M displayed on the display unit 20, it can be determined that when the moisture content is low and the temperature is normal, the subject has minor dehydration, whereas when the moisture content is normal and the temperature is normal, the subject is healthy. In contrast, it can be roughly determined by the doctor that when the moisture content is low and the temperature is high, the subject has severe dehydration, whereas when the moisture content is normal and the temperature is high, the subject has an illness other than dehydration such as a cold.

The embodiment of the moisture meter according to the present invention is a moisture meter that measures a moisture content of a subject, including an impedance-type moisture measuring unit that is held in an armpit of the subject so as to measure a moisture content of the subject, the impedance-type moisture measuring unit including a measurement current supply electrode portion and a voltage measurement electrode portion that make contact with a skin surface of the armpit. Due to this, the moisture meter can easily measure the moisture content of the subject and can be used effectively as means for assisting the subject in regulating an appropriate moisture content. The reason for selecting the armpit as the location of the living body where the moisture content of the subject can be appropriately measured using the moisture meter and measuring the moisture content in the armpit R is because the moisture content in the armpit R reflects the moisture state of the entire living body of the subject M.

Preferably, the moisture meter includes a temperature measuring unit that is held in the armpit of the subject to measure the temperature of the subject. Due to this, by measuring the temperature of the subject simultaneously with measuring the moisture content of the subject in the armpit of the subject, the subject state can be determined using the correlations between the moisture content and the temperature.

Preferably, the moisture meter includes a main body, a measuring unit holder that is disposed at one end of the main body and is sandwiched in the armpit while holding the impedance-type moisture measuring unit and the temperature measuring unit, and a display unit holder that is disposed at the other end of the main body to hold a display unit that displays the measured moisture content of the subject and the measured temperature of the subject. Due to this, the main body has such a shape that the subject M can easily hold or grip with the hand, the display unit holder can protrude to the front side from the armpit in a state where the measuring unit holder is sandwiched in the armpit, and the person who makes measurements can read the moisture content and temperature displayed on the display unit with the naked eyes.

Preferably, a plurality of the temperature measuring units is held on the measuring unit holder. According to this configuration, it is possible to obtain the average of the measured temperature values using a plurality of temperature measuring units and to obtain more accurate moisture content and temperature.

Preferably, each of the electrode portions of the impedance-type moisture measuring unit includes an electrode terminal for making direct contact with the skin surface of the armpit, and an elastically deformable member for pressing the electrode terminal against the skin surface of the armpit. In this manner, when measuring the moisture content and temperature, the electrode terminal can be reliably brought into contact with the skin surface of the armpit.

Preferably, each of the electrode portions of the impedance-type moisture measuring unit includes an electrode terminal for making direct contact with the skin surface of the armpit, and a sticking member for making close contact with the skin surface of the armpit to press the electrode terminal against the skin surface of the armpit. In this manner, when measuring the moisture content and temperature, the electrode terminal can be reliably brought into contact with the skin surface of the armpit.

Figure 9:
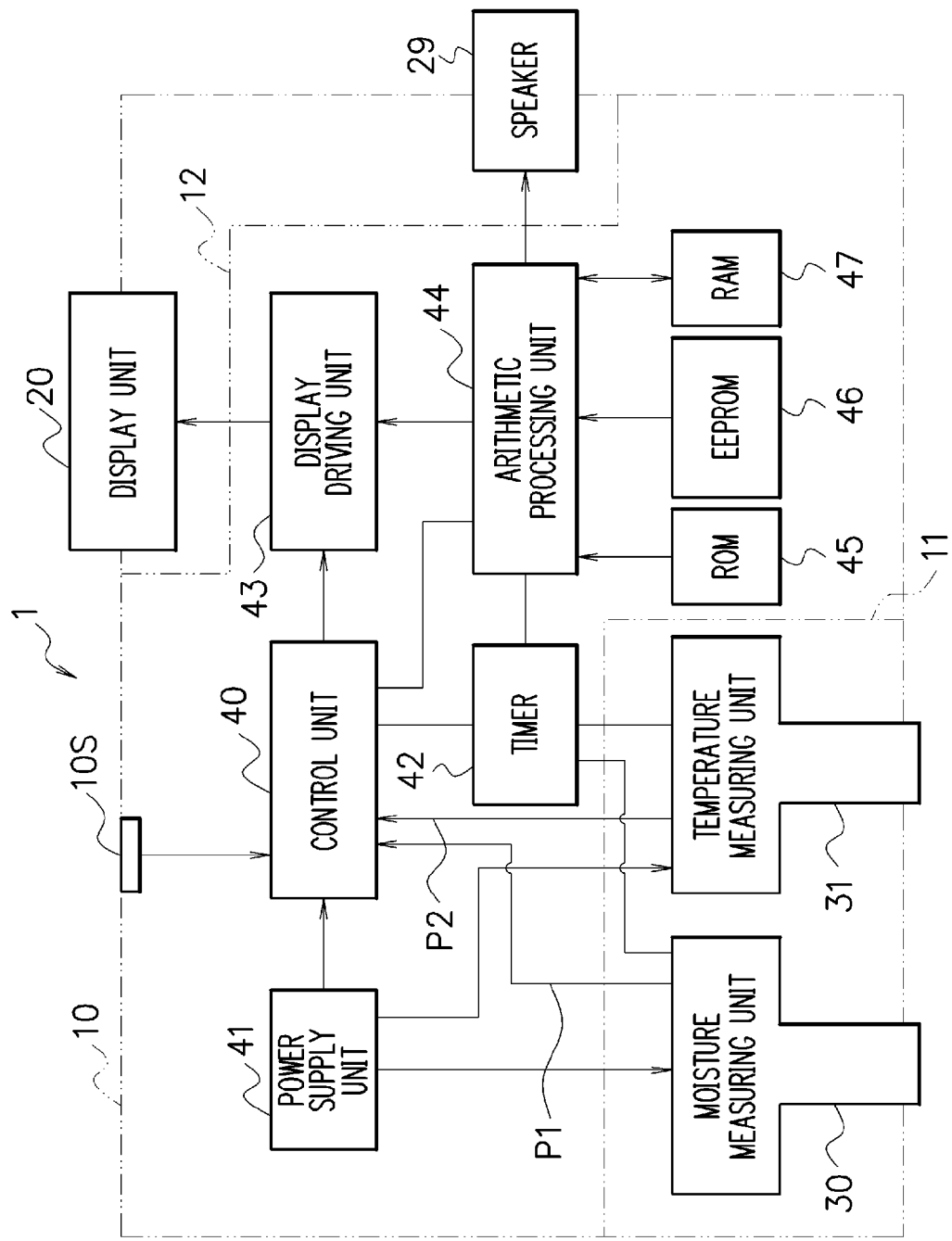
FIG. 9 is a block diagram showing a configuration example of a still another embodiment of the present invention.

FIG. 9 is a block diagram showing a configuration of a still another embodiment of the moisture meter.

Figure 10:
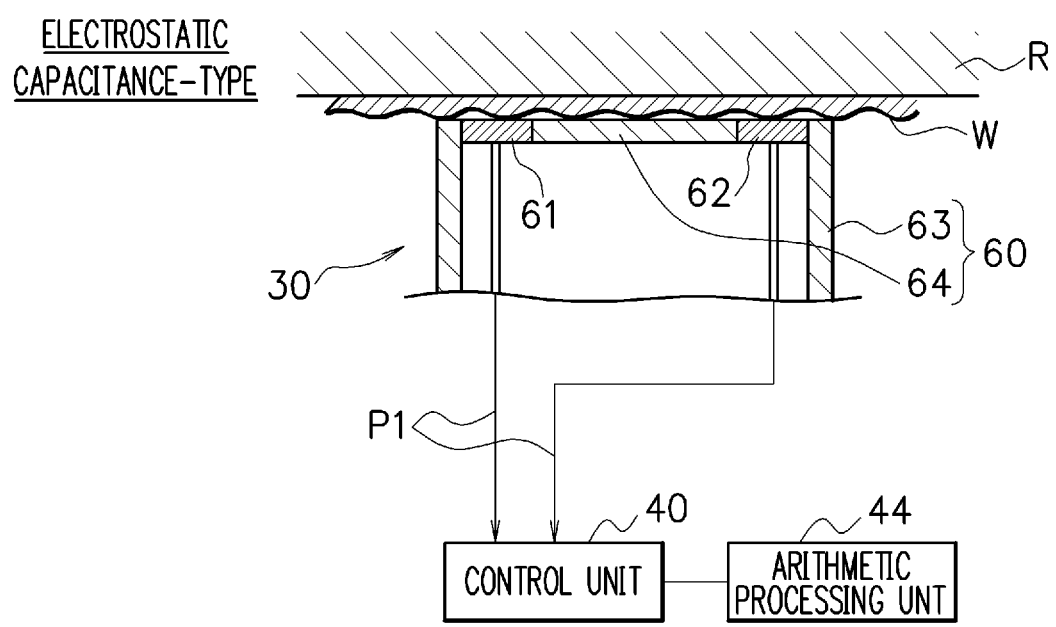
FIG. 10 is an explanatory diagram showing a configuration of a moisture measuring unit shown in FIG. 9.

In FIG. 9, constituent elements denoted by the same reference numerals as those of FIG. 3 have the same structure, and the present embodiment is different in that the configuration of a moisture measuring unit 30 uses electrostatic capacitance as shown in FIG. 10. Hereinafter, the description of FIG. 3 will be incorporated in the description of the same constituent elements, and the difference will be described mainly.

The moisture measuring unit 30 shown in FIG. 9 has a configuration as shown in FIG. 10.

That is, the moisture measuring unit 30 measures the electrostatic capacitance of the living body of a subject M which is a measurement target object to measure the moisture content based on a variation in permittivity that changes with a moisture content ratio. The moisture measuring unit 30 includes a container portion 60 and two electrodes 61 and 62. The container portion 60 includes a circumferential portion 63 made from a resin and a lid portion 64, and the two electrodes 61 and 62 are disposed so as to exposed to the outside from the lid portion 64 in a state where the electrodes 61 and 62 are separated from the lid portion 64 and are electrically isolated from each other. In this manner, when the two electrodes 61 and 62 make contact with the skin of the armpit R and the moisture W on the speaker, the electrostatic capacitance of the living body of the subject M is measured, whereby the moisture content is measured based on a variation in the permittivity that changes with a moisture content ratio. A moisture content data signal P1 from the two electrodes 61 and 62 is delivered to the control unit 40, and the arithmetic processing unit 44 calculates the moisture content based on the moisture content data signal P2.

In this manner, the moisture measuring unit 30 detects the electrostatic capacitance using the plurality of electrodes 61 and 62 to measure the moisture content based on a variation in the permittivity that changes with a moisture content ratio. Thus, it is possible to measure the moisture content in the armpit of the subject based on the electrostatic capacitance. The electrostatic capacitance can be calculated by the following equation. Given that "S" and "d" take constant values, the electrostatic capacitance (C) is proportional to the value of permittivity ($\epsilon$), and the larger the moisture content, the greater become the values of the permittivity and the electrostatic capacitance.

Electrostatic Capacitance$(C)=\epsilon \times S/d(F)$

Permittivity=$\epsilon$
S=Size of Sensor Surface
d=Distance between Electrodes

In this manner, the arithmetic processing unit 44 estimates and calculates the moisture content and temperature of the subject based on a change over time of the moisture content data and temperature data of the subject, obtained from the moisture content data P1 measured by the moisture measuring unit 30 and the temperature data P2 measured by the temperature measuring unit 31.

Thus, the measurement using electrostatic capacitance is simple because it is only necessary to prepare two electrodes electrically isolated from each other, and it is not necessary to prepare each pair of measurement current supply electrode portions and voltage measurement electrode portions unlike the impedance-type moisture meter.

Figure 11:
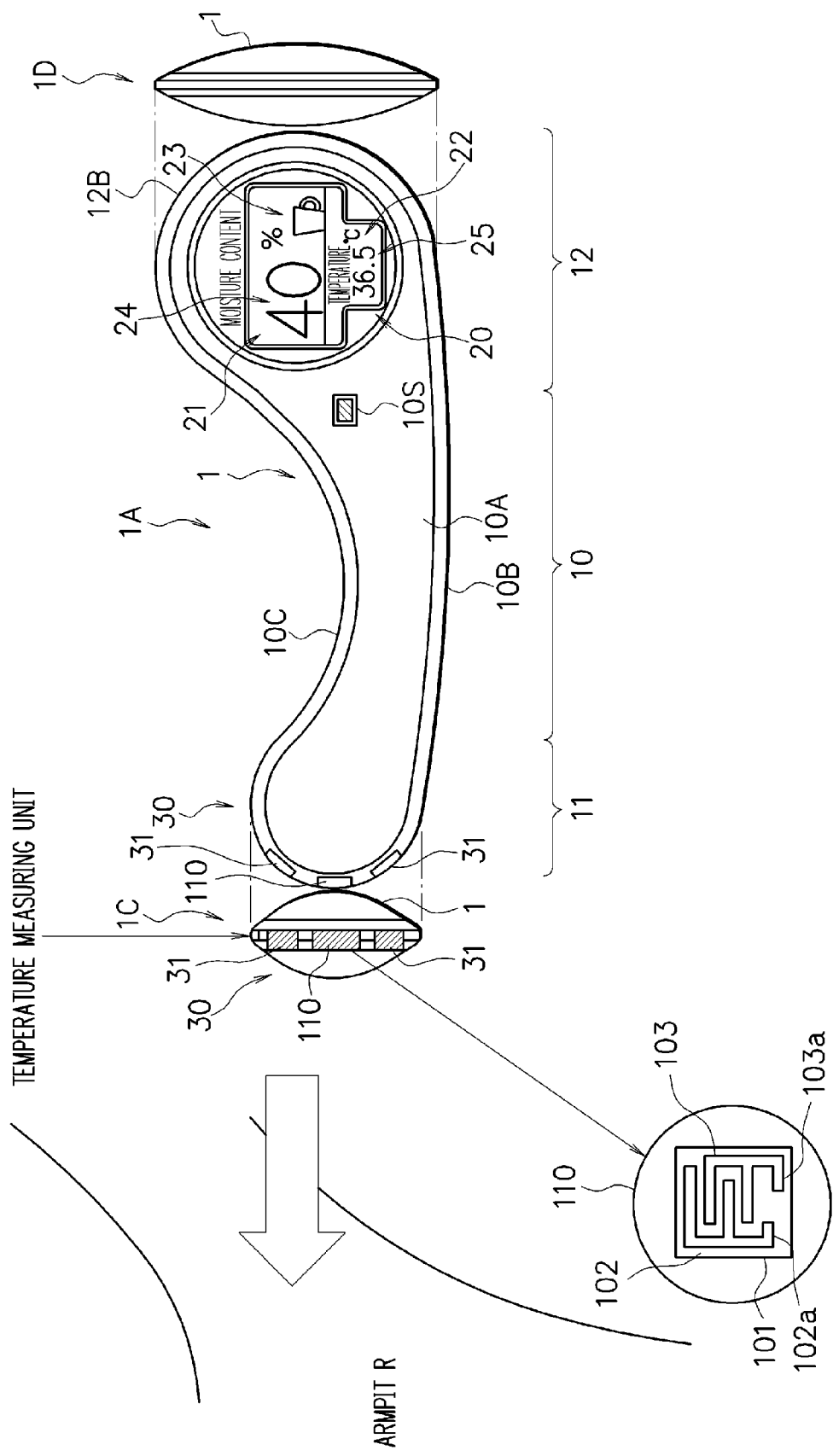
FIG. 11 is a diagram showing a modification of the electrode structure of an embodiment of the moisture meter according to the present invention.

FIG. 11 shows a modification of an electrode structure.

This electrode structure can be used for both the impedance-type moisture meter and the electrostatic capacitance-type moisture meter.

First, the impedance-type moisture meter will be described.

As shown in FIG. 11, an electrode portion 110 has such a structure that it is exposed to the left side surface of the moisture meter 1 that is illustrated in FIG. 2C.

The electrode portion 110 is configured to include a base portion 103 formed of a rectangular insulator, for example, and interdigital electrodes 102 and 103 formed of a linear conductor and formed on the surface of the base portion 103 so as to face with a small gap therebetween. Terminal portions 102a and 103a are formed at the respective ends of the interdigital electrodes 102 and 103.

When the interdigital electrode 102 is used as the first voltage measurement electrode portion and the interdigital electrode 103 is used as the second voltage measurement electrode portion, it is possible to measure the moisture content based on the impedance by supplying a predetermined driving current from a power supply unit to the terminal portions of the respective electrode portions.

Just by using the interdigital electrode structure described in FIG. 11, that is, by using the interdigital electrodes 102 and 103 only, as well as without forming the first and second measurement current supply electrode portions 30A and 30B and the first and second voltage measurement electrode portions 100A and 100B, the moisture content may be measured based on the electrostatic capacitance.

In this case, when the two interdigital electrodes 102 and 103 are disposed to face each other with a small gap therebetween as shown in the figure, and a current is applied to one of the electrodes, the moisture as a substance to be detected is oxidized, and the oxidized substance is reduced to the original substance in the other electrode. That is, by allowing oxidation and reduction to repeatedly occur in two electrodes, it is possible to detect the moisture as a substance to be detected. In this case, preferably, detection is performed in a dual mode.

To realize dual-mode detection, specifically, oxidation potential for moisture is applied from the power supply unit shown in FIG. 9 to the interdigital electrode 102, and reduction potential is applied to the other interdigital electrode 103. As a result, in the dual mode, a so-called Redox cycle in which oxidation and reduction occur repeatedly takes place, and detection sensitivity can be improved by increasing current.

As for a substrate 101 which is an insulating substrate in FIG. 11, a substrate of which the substrate or the entire body has insulating properties may be used as an electrode substrate, and for example, a silicon substrate including an oxide film, a quartz substrate, an aluminum oxide substrate, a glass substrate, a plastic substrate, or the like can be used. As conductor ideal as the material of electrodes, metals such as gold, platinum, silver, chromium, titanium, or stainless steel, semiconductors, conductive carbon, conductive ink, or the like can be used.

The electrode portions can be manufactured by a method of depositing the above-mentioned conductor metals on the insulating substrate 101 as a thin film according to a method such as evaporation, sputtering, chemical vapor deposition (CVD), or the like and patterning the thin film into the shape of interdigital electrodes according to a photolithography method, for example. In addition to the photolithography, interdigital electrodes may be printed with conductive ink on the substrate 101 which is an insulating material using an ink jet printer or the like.

The use of such an electrode structure enables the moisture measuring unit 30 to make contact with the deepest portion of the armpit R.

The present invention is not limited to the above embodiment. Various changes can be made to the present invention, and various modifications can be made within the scope described in the claims.

In the illustrated example, one moisture measuring unit 30 and one temperature measuring unit 31 are disposed in the measuring unit holder 11.

However, the present invention is not limited to this, and as shown in FIGS. 8A through 8D, a plurality of temperature measuring units 31 may be disposed in the measuring unit holder 11. According to this configuration, it is possible to further improve temperature measurement accuracy by averaging the temperature values obtained by the temperature measuring units 31.

REFERENCE SIGNS LIST

1: MOISTURE METER
10: MAIN BODY
11: MEASURING UNIT HOLDER
12: DISPLAY UNIT
M: SUBJECT

R: ARMPIT
11: MEASURING UNIT HOLDER
12: DISPLAY UNIT HOLDER
12: DISPLAY UNIT HOLDER
20: DISPLAY UNIT
30: MOISTURE MEASURING UNIT
30A, 30B: MEASUREMENT CURRENT SUPPLY ELECTRODE PORTION
31: TEMPERATURE MEASURING UNIT
100A, 100B: VOLTAGE MEASUREMENT ELECTRODE PORTION
110: ELECTRODE PORTION

The invention claimed is:

1. A moisture meter for measuring a moisture content of a subject, comprising:
   a main body possessing one end, an other end opposite to the one end, and an intermediate portion extending between the one end and the other end, the main body also possessing a thickness between opposite surfaces of the main body that partially contact skin surface of the user during use of the moisture meter;
   a measuring unit holder at the one end of the main body configured to be held in an armpit of the subject;
   an impedance-type moisture measuring unit mounted on the measuring unit holder, the impedance-type moisture measuring unit including a measurement current supply electrode portion and a voltage measurement electrode portion that make contact with the skin surface of the armpit to provide information used to measure the moisture content of the subject when the measuring unit holder is held in the armpit;
   a display unit holder at the other end of the main body;
   a display unit mounted on the display unit holder and configured to display the measured moisture content of the subject;
   the intermediate portion of the main body including a first curved portion that is curved outward to form a convex surface along one side of the intermediate portion of the main body and a second curved portion that is curved inward to form a concave surface along a side of the intermediate portion of the main body that is opposite the one side of the intermediate portion of the main body, the first and second curved portions being located between the display unit and the impedance-type moisture measuring unit, the second curved portion possessing a greater radius of curvature than the first curved portion; and
   the display unit holder at the other end of the main body extending from the subject when the measuring unit holder at the one end of the main body is held in the armpit of the subject, allowing the subject to read the measured moisture content on the display unit while the measuring unit holder at the one end of the main body is held in the armpit.

2. The moisture meter according to claim 1, further comprising:
   a temperature measuring unit mounted on the measuring unit holder that is configured to be held in the armpit of the subject to measure temperature of the subject.

3. The moisture meter according to claim 1, wherein a plurality of temperature measuring units is held in the measuring unit holder.

4. The moisture meter according to claim 1, wherein each of the electrode portions of the impedance-type moisture measuring unit includes an electrode terminal for making direct contact with the skin surface of the armpit, and an elastically deformable member for pressing the electrode terminal against the skin surface of the armpit.

5. The moisture meter according to claim 1, wherein each of the electrode portions of the impedance-type moisture measuring unit includes an electrode terminal for making direct contact with the skin surface of the armpit, and a sticking member for making close contact with the skin surface of the armpit to press the electrode terminal against the skin surface of the armpit.

6. A moisture meter for measuring a moisture content of a subject, comprising:
   a main body extending from a proximal end to a distal end;
   a measuring unit holder at the proximal end of the main body configured to be held in an armpit of the subject;
   an electrostatic capacitance-type moisture measuring unit mounted on the measuring unit holder to provide information used to measure the moisture content of the subject when the measuring unit holder is held in the armpit;
   the moisture measuring unit detects an electrostatic capacitance using a plurality of electrodes to measure the moisture content based on a variation in permittivity that changes with a moisture content ratio;
   a display unit holder at the distal end of the main body;
   a display unit mounted on the display unit holder and configured to display the measured moisture content of the subject measured;
   the main body including a first curved portion that is curved outward to form a convex surface and a second curved portion that is curved inward to form a concave surface, the second curved portion possessing a greater radius of curvature than the first curved portion; and
   the first curved portion extending along one side of the main body at a location between the moisture measuring unit at the proximal end of the main body and the display unit at the distal end of the main body, the second curved portion extending along an other side of the main body at a location between the moisture measuring unit at the proximal end of the main body and the display unit at the distal end of the main body, the one side of the main body and the other side of the main body being positioned opposite one another.

7. The moisture meter according to claim 6, further comprising:
   a temperature measuring unit that is mounted on the measuring unit holder configured to be held in the armpit of the subject to measure temperature of the subject.

8. The moisture meter according to claim 6, wherein a plurality of temperature measuring units is held in the measuring unit holder.

9. The moisture meter according to claim 6, wherein each of the electrode portions of the electrostatic capacitance-type moisture measuring unit includes an electrode terminal for making direct contact with the skin surface of the armpit, and an elastically deformable member for pressing the electrode terminal against the skin surface of the armpit.

10. The moisture meter according to claim 6, wherein each of the electrode portions of the electrostatic capacitance-type moisture measuring unit includes an electrode terminal for making direct contact with the skin surface of the armpit, and a sticking member for making close contact with the skin surface of the armpit to press the electrode terminal against the skin surface of the armpit.

11. The moisture meter according to claim 1, wherein the measuring unit holder has one convex portion and an other convex portion opposite to the one convex portion.

12. The moisture meter according to claim 6, wherein the measuring unit holder has one convex portion and an other convex portion opposite to the one convex portion.

* * * * *